(12) United States Patent
Fita

(10) Patent No.: US 8,609,722 B2
(45) Date of Patent: Dec. 17, 2013

(54) ANESTHETIC COMPOSITION FOR TOPICAL ADMINISTRATION COMPRISING LIDOCAINE, PRILOCAINE AND TETRACAINE

(76) Inventor: Fernando Bouffard Fita, Barcelona (ES)

( * ) Notice: Subject to any disclaimer, the term of this patent is extended or adjusted under 35 U.S.C. 154(b) by 1459 days.

(21) Appl. No.: 10/562,392

(22) PCT Filed: Jun. 1, 2004

(86) PCT No.: PCT/EP2004/050967
§ 371 (c)(1),
(2), (4) Date: Dec. 19, 2005

(87) PCT Pub. No.: WO2004/110423
PCT Pub. Date: Dec. 23, 2004

(65) Prior Publication Data
US 2006/0140986 A1    Jun. 29, 2006
US 2007/0269465 A9    Nov. 22, 2007

(30) Foreign Application Priority Data
Jun. 19, 2003    (ES) .................................. 200301548

(51) Int. Cl.
*A61K 31/24*    (2006.01)
*A61K 9/00*    (2006.01)

(52) U.S. Cl.
USPC .......................................... 514/537; 424/400

(58) Field of Classification Search
USPC .......................................... 424/400; 514/537
See application file for complete search history.

(56) References Cited

U.S. PATENT DOCUMENTS

| 4,529,601 A | 7/1985 | Broberg et al. |
| 5,750,139 A * | 5/1998 | Lutz et al. .................... 424/448 |
| 5,863,941 A | 1/1999 | Liedtke |
| 5,993,836 A | 11/1999 | Castillo |
| 2002/0006435 A1 * | 1/2002 | Samuels et al. ............... 424/449 |
| 2002/0128285 A1 | 9/2002 | Cassel |
| 2002/0137813 A1 | 9/2002 | Bond et al. |
| 2003/0103955 A1 * | 6/2003 | Santana et al. ............... 424/94.2 |

FOREIGN PATENT DOCUMENTS

| EP | 0002425 A | 6/1979 |
| JP | 54101414 A | 8/1979 |
| JP | 2001521888 A | 11/2001 |
| JP | 2003510259 A | 3/2003 |
| WO | WO9922717 A1 | 5/1999 |
| WO | WO0122907 A1 | 4/2001 |
| WO | WO 0154679 A | 8/2001 |

OTHER PUBLICATIONS

PCT Notification concerning Transmittal of International Application as Published PCT/EP2004/050907 International Search Report.
Leopold C.S. et al, "Effect of Cutaneously Applied Nonionic Surfactants and Local Anesthetic Bases on Thermal Sensations," Die Pharmazie, Jan. 2004, pp. 50-54, vol. 59, No. 1.
Maria Dolores Carceles, Amethocaine-Lidocaine Cream, a New Topical Formulation for Preventing Venopuncture-Induced Pain in Children, Regional Anesthesia and Pain Medicine, May-Jun. 2002, pp. 289-295, vol. 27, No. 3.

* cited by examiner

*Primary Examiner* — Sreeni Padmanabhan
*Assistant Examiner* — Jody Karol
(74) *Attorney, Agent, or Firm* — Peter B. Scull; Hamilton, DeSanctis & Cha LLP

(57) ABSTRACT

Compositions having a mixture of lidocaine, prilocaine and tetracaine, or their pharmaceutically acceptable salts. A preferred composition includes the following components in the indicated approximate w/w percentages: 1.5% lidocaine base; 1.5% prilocaine base; 4% tetracaine base and water. In some implementations, also included may be about 10% methylpynrolidone; 2% dimethyl sulfoxide; 0.08% topical hyaluronidase; 1.5% guar gum; 1% polyoxyethylenesorbitan monolaurate; 0.5 polyoxyethylenesorbitan monooleate, and water to 100%. Such compositions exhibits a high concentration on skin, a deep anesthetic effect and a significantly more rapid onset of the anesthetic effect than comparable transdermal anesthetics.

23 Claims, No Drawings

ANESTHETIC COMPOSITION FOR TOPICAL ADMINISTRATION COMPRISING LIDOCAINE, PRILOCAINE AND TETRACAINE

CROSS-REFERENCE TO RELATED APPLICATIONS

The present invention is the US national stage of the Patent Cooperation Treaty (PCT) Application Number PCT/EP2004/050967 filed 1 Jun. 2004, entitled "Anesthetic Composition for Topical Administration Comprising Lidocaine, Prilocaine and Tetracaine"; which designated all states including the United States of America; the subject matter of which hereby being specifically incorporated herein by reference for all that it discloses and teaches, and claiming priority from Spanish Application Number P200301548, filed 19 Jun. 2003; the subject matter of which also hereby being specifically incorporated herein by reference for all that it discloses and teaches.

This invention relates to the field of human medicine, and specifically to topical anesthetic formulations which include mixtures of several anesthetic agents.

BACKGROUND ART

Surgical techniques can only be performed after the highly sensitive nerve endings in the skin are anesthetized. Anesthetic agents are pharmacologically active agents that block nerve impulses conduction in sensory and motor nerve fibers when applied in therapeutically effective amounts. Their action is reversible, their use being followed by the complete recovery in nerve function with no evidence of structural damage to nerve fibers or cells.

To be effective, a topical anesthetic should contain sufficient concentration of the active agent to produce an anesthetic effect, it should penetrate intact skin sufficiently to deliver a therapeutic dose, it should exhibit a rapid onset of anesthetic action and have a prolonged anesthetic effect. Potency of anesthetics in clinical situations depends on both their ability to reach the nerve fibers and their intrinsic blocking activities. Factors such as nerve penetration, vascular absorption, and local tissue binding are all of them determinants for anesthetic potency.

Local anesthetics are traditionally injected into the desired site with a syringe. Most formulations of local anesthetics are aqueous solutions designed for injection into tissue, around nerves, or into the epidural spaces. The use of syringe is disadvantageous because the needle itself causes pain on penetration, the volume of anesthetic dissolution can cause stretching at the site (also causing pain), and furthermore preservatives contained in the aqueous dissolution can cause stinging at the wound site. Pain relief is especially important in the area of pediatrics, where even minimal pain may result in an anxious and uncooperative patient.

It is known the use of topical anesthetics. Transdermal delivery is advantageous over intravenous delivery because the former avoids risks associated with parenteral treatment and eliminates gastrointestinal adverse effects due to pharmaceutical active ingredients, preservatives, etc. However, the use of transdermal anesthetics (i.e. through the skin) is often problematic, and fluid and in gel compositions have often proven unsuccessful.

The amide of formula (I), known as lidocaine, has a melting point of 68-69° C. and it is the most commonly used local anesthetic, especially in the form of aqueous dissolutions of its hydrochloride, which are administered intravenously or topically, as jelly, ointment or spray (cf. U.S. Pat. No. 2,441,498). Unfortunately, when administered topically, these formulations are not effectively absorbed transdermally, but only through mucosal surfaces.

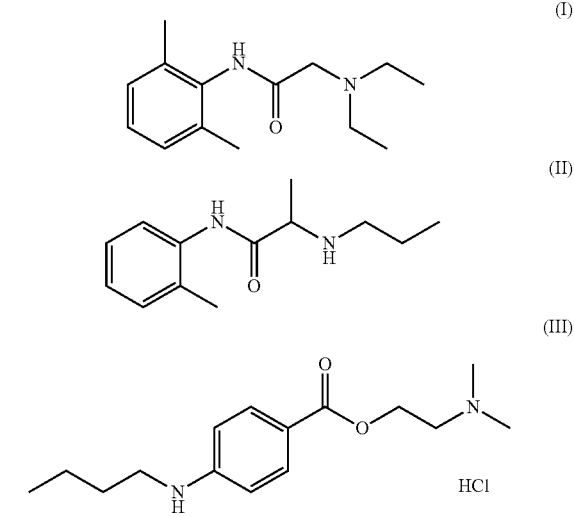

The amide of formula (II), known as prilocaine, is a local anesthetic agent which takes the form of crystalline needles having a melting point of 37-38° C. (cf. GB 839.943-A). Its hydrochloride is crystallized from ethanol and isopropyl ether and it is readily soluble in water. Unfortunately, methemoglobinaemia and cyanosis appear to occur more frequently with prilocaine than with other local anesthetics. Methemoglobinaemia is a disease state of the erythrocyte consisting in the formation of oxidized iron compound in the heme protein of the erythrocyte. Symptoms usually occur when doses of prilocaine hydrochloride exceed about 8 mg per kg body-weight although the very young may be more susceptible. This fact severely limits the size of the area to be anesthetized.

Enhancement of drug absorption through the skin has been a challenge for researchers for many years. Research has been also focused on finding effective topical formulations of an anesthetic which provide a rapid onset and a long duration of anesthesia. When applied onto intact skin, currently available topically used anesthetic preparations are generally ineffective or only partially effective.

One approach to the prolongation of anesthesia involves the combination of topical anesthetics with a vasoconstrictor, but also involves considerable adverse side effects. Another approach involves the combination of several anesthetic agents and different topical excipients (cf. e.g. EP 43.738-A, WO 9633706-A). In fact, at present, the most successful commercially available preparation for dermal anesthesia is the lidocaine-prilocaine cream named EMLA (a registered trademark in some countries) of Astra Lakemedel AB, Sweden (cf. U.S. Pat. No. 4,562,060). In some clinical tests, EMLA cream has been found preferable to lidocaine or to ethylchoride. EMLA is an oil-in-water emulsion in which the organic phase is an eutectic mixture of lidocaine and prilocaine bases (2.5% and 2.5% by weight) in water which is thickened with carbomer (Carbopol®). An eutectic mixture has a melting point lower than the one of any of its ingredients. EMLA cream is applied as a thick layer under an occlusive or semiocclusive dressing for inducing a rapid absorption through the skin.

A major inconvenience of EMLA is that its onset time for anesthesia is relatively long, approximately one hour or more. This onset time is not very practical for several clinical procedures. For more invasive procedures such as split skin graft harvesting, EMLA has to be applied at least two hours prior to surgical operation. Such delay is a problem for both patients and for medical staff, particularly in the area of pediatrics. Moreover, EMLA is formulated at pH 9.0 to incorporate the anesthetic agents in base form. The skin, which has an acidic pH (5 to about 5.5) is sensitive to such a high basic pH and significant skin irritation can occur. Dermal application of EMLA may cause a transient, local blanching followed by a transient, local redness or erythema. Another disadvantage of EMLA is that for deep penetrative effect it is necessary that the cream is applied under occlusive dressing.

There have been several attempts trying to improve EMLA cream. One example are topical anesthetic compositions which additionally include a vasodilator. A formulation including lidocaine base, prilocaine hydrochloride, dibucaine, a vasodilator and carrier is described in the patent application WO 01/54679-A. Another example is the topical anesthetic composition comprising an eutectic mixture of lidocaine and prilocaine in a lipophilic base described in the U.S. Pat. No. 5,993,836. It has been reported that this anesthetic formulation has significantly more rapid onset than similar transdermal anesthetics, such as EMLA cream.

Tetracaine hydrochloride (amethocaine) is a local anesthetic of the ester type with formula (III) (cf. U.S. Pat. No. 1.889.645). There are many topical formulations in the market containing tetracaine hydrochloride, one of them is AME-TOP of T.J. Smith & Nephew Limited, England (cf. GB 2.258.397-A) which contains 40 mg of active ingredient (4%, w/w), an aqueous gelling agent and a pharmaceutically acceptable salt.

Thus, it appears to be highly desirable to have a topical anesthetic composition which provides a rapid and deep anesthesia, with a high concentration on skin. In particular, it would be desirable to have a topical anesthetic with the benefits of lidocaine and prilocaine, but free of the above-described limitations associated therewith.

SUMMARY OF THE INVENTION

It has now been surprisingly found that a topical anesthetic composition comprising a mixture of lidocaine, prilocaine and tetracaine, exhibit a significantly more rapid onset of the anesthetic effect than comparable transdermal anesthetics, such as EMLA cream.

Thus, an aspect of the present invention relates to a pharmaceutical composition for topical administration comprising: (i) a therapeutically safe and effective amount of lidocaine or of a pharmaceutically acceptable salt thereof; (ii) a therapeutically safe and effective amount of prilocaine or of a pharmaceutically acceptable salt thereof, and (iii) a therapeutically safe and effective amount of tetracaine or of a pharmaceutically acceptable salt thereof.

In a particular embodiment the composition further comprises water. When tetracaine is as its hydrochloride, it can be dissolved in water and added to the previously prepared mixture of lidocaine and prilocaine. When tetracaine is as such, water is not necessary, so tetracaine can be added to the mixture of lidocaine and prilocaine directly. Optionally, the mixture of lidocaine, prilocaine and tetracaine can also be dissolved in alcohols (e.g. ethanol, isopropanol and mixtures thereof).

In another embodiment, lidocaine or its salt on the one side, and prilocaine or its salt on the other side, form an eutectic mixture. As an eutectic mixture, the compositions remain liquid at room temperature and the penetration through the skin is enhanced, giving as a result, a shorter time of effect establishment, a higher efficacy and less adverse effects. Particularly, lidocaine or its salt can be in an amount from about 0.5% to about 5%, w/w, and prilocaine or its salt can be in an amount from about 0.5% to about 5%. More particularly, lidocaine, prilocaine, or their salts are in an amount of about 1.5%, w/w. On the other hand, tetracaine or its salt can be in an amount from about 0.5% to about 8%, w/w, and more particularly, in an amount of about 4%, w/w.

In another embodiment, the pharmaceutical composition further comprises appropriate amounts of pharmaceutically acceptable excipients to constitute a topical formulation. The composition can comprise different types of excipients: skin penetration enhancers, spreading agents, viscosity increasing agents, surfactants and preservatives. Optionally, other components can be added to the compositions of this invention in appropriate amounts to enhance their pharmaceutical acceptability, as it will be obvious to a person skilled in the art.

The composition can comprise at least one skin penetration enhancer which enhances dermal absorption of the active ingredients by reversibly altering the barrier of skin. Preferred skin penetration enhancer agents that may be used are dipolar aprotic solvents as methylpyrrolidone and dimethyl sulfoxide (DMSO) which are rapidly absorbed through the skin and enhance dermal absorption of many other chemicals. In a particular embodiment, methylpyrrolidone is in an amount from about 5% to about 20%, w/w. In a more particular embodiment, methylpyrrolidone is in an amount of about 10%, w/w. In another particular embodiment, the skin penetration enhancer is dimethyl sulfoxide (DMSO), which is in an amount from about 0.5% to about 5%, w/w, and more particularly in an amount of about 2%, w/w.

The composition can comprise at least one spreading agent, which facilitates uniform spread of anesthetic agents. In particular embodiments, the spreading agent is selected from hyalurodinases and/or derivatives of mucopolysaccharidases. They prevent the elevation of extracellular tissue pressure and also prevent focal accumulations of local anesthetic agents, which at high enough levels may cause neurotoxic damage.

The composition can further comprise at least one viscosity increasing agent, also known as thickening agents. Thickeners that may be used include those known to one skilled in the art, such as hydrophilic and hydroalcoholic gelling agents frequently used in cosmetics, food products and pharmaceutical formulations. Preferably, a commercial carbomer will be used, Carbopol N-940. Another preferred gelling polymer includes guar gum. In particular embodiments, the viscosity increasing agent is in an amount from about 0.5% to about 2%, w/w.

The composition can comprise at least one surfactant, also known as emulsifier. These compounds are widely used in the preparation of stable pharmaceutical, cosmetic and food emulsions. In a preferable embodiment the surfactant is a non-ionic surfactant and in a more particular embodiment, polysorbates are used (e.g. polysorbate 20 and 80).

The compositions of the present invention may be prepared and packaged under sterile conditions. Alternatively, at least one suitable antimicrobial agent may be incorporated into the formulations as preservatives. Some known preservatives useful in this invention include methylparaben and propylparaben in their acidic form or as sodium salts.

The topical formulations of the present invention may be made into a wide variety of product forms, as it is well known in the art. These include, among others, lotions, creams, gels, sticks, sprays, ointments and pastes. In order to facilitate the application of the compositions, they can be, for instance, in a dispenser or on the surface of a dressing, a patch or a pad. These product forms may comprise several types of carriers including, among others, dissolutions, aerosols, emulsion gels, solids and liposomes.

Another aspect of the present invention relates to a pharmaceutical composition for topical administration comprising the following components in the indicated approximate w/w percentages: 1.5% of lidocaine base; 1.5% of prilocaine base; 4% of tetracaine base; 10% of methylpyrrolidone; 2% of dimethyl sulfoxide; 0.08% of topical hyaluronidase; 1.5% of guar gum; 1% of Tween® 20 (polyoxyethylenesorbitan monolaurate; CAS No: 9005-64-5); 0.5% of Tween® 80 (polyoxyethylenesorbitan monooleate, CAS No: 9005-65-6), and the necessary amount of water to 100%.

The application of the compositions of the present invention comprises contacting an area of skin with a thin layer of the composition. When an intravenous device is used, the application of the compositions of the present invention will be preferably at its site of insertion. The composition is allowed to act for an appropriate time for the onset of anesthesia. The term "onset of anesthesia" means the time until peak effect on the nerve endings. For the compositions of the present invention, this time is shorter than with other commercial compositions. In a preferred method of using, three consecutive applications may be done: a first application followed by ten minutes of resting to achieve the anesthetic effect; a second application followed by ten minutes more, and a third application followed by five minutes of resting. After these twenty-five minutes in all, the composition can be removed and the surgical operation can be done or the medical device can be inserted. The duration of anesthetic effect for the compositions of the present invention is from about one to about five hours, depending on the subject metabolism. The effect is much more durable and increases in time compared with other available compositions.

In addition to the rapid onset, the formulations of the present invention are advantageous for not depending on the application of an occlusive or a semiocclusive dressing for getting a rapid absorption through the skin. Even if it is not necessary, occlusion may be applied. The compositions of the invention may be applied directly to the skin or by the use of transdermal treatment systems, including patches or pads, which are semipermeable membranes with the active compound applied to the surface.

The compositions of the present invention are particularly useful before superficial dermatological treatments. These include, among others, surface verruca extirpation, infiltrations or molluscum extraction. The same applies before esthetic treatments such as peelings, filling micropuncture of wrinkles, laser or application of facial filling; and before the insertion of a medical device.

The term "safe and effective amount" as used herein, means an amount of an active ingredient or a composition high enough to deliver the desired skin benefit, but low enough to avoid serious side effects within the scope of medical judgment. The term "pharmaceutically acceptable" as used herein, means suitable for use in contact with the tissues without undue toxicity, irritation, incompatibility, instability, allergic response, and the like. All numerical ranges used herein, are meant to be inclusive of their upper and lower limits. Unless noted otherwise, all percentages in the compositions of the invention are on a weight-to-weight basis. Throughout the description and claims the word "comprise" is not intended to exclude other technical features, additives, components, or steps. The abstract of this application is incorporated herein as reference. Additional objects, advantages and features of the invention will become apparent to those skilled in the art upon examination of the description or may be learned by practice of the invention. The following particular embodiments are provided by way of illustration, and is not intended to be limiting of the present invention.

DETAILED DESCRIPTION OF PARTICULAR EMBODIMENTS

Preparation of the Composition

Tubes of 30 g were prepared with the composition per tube described in the following table:

| Component | % (w/w) |
|---|---|
| Dissolution A | |
| Distilled water | 31.82% |
| Nipagin M-Ac | 0.08% |
| Nipasol M-Ac | 0.02% |
| Tween ® 20 (polyoxyethylenesorbitan monolaurate; CAS No: 9005-64-5) | 1.00% |
| Guar gum | 1.50% |
| Dissolution B | |
| Tetracaine HCl | 4.00% |
| Distilled water | 45.00% |
| Dissolution C | |
| Lidocaine base | 1.5% |
| Prilocaine base | 1.5% |
| Dissolution D | |
| Distilled water | 1.00% |
| Topical hyaluronidase | 0.08% |
| Dissolution E | |
| Tween ® 80 (polyoxyethylenesorbitan monooleate, CAS No: 9005-65-6) | 0.50% |
| Dissolution F | |
| Methylpyrrolidone | 10% |
| Dissolution G | |
| DMSO | 2.00% |

Lidocaine base and prilocaine base were weighed and sieved through a 2 mm mesh. Components of dissolutions A, B, D, E, F and G were weighed separately. The amounts of required distilled water for each dissolution were also prepared in 100 mL recipients. Distilled water for dissolution A was heated in an appropriate recipient and Nipagin and Nipasol were added until dissolved. The mixture was left to cool. Then, Tween® 20 (polyoxyethylenesorbitan monolaurate; CAS No: 9005-64-5) was added and the mixture was shacked with a stripping knife without lathering. Guar gum was added to the mixture and shacked during ten minutes with a glass stick. In the 100 mL recipient containing distilled water, tetracaine HCl was added and it was dissolved with a magnetic agitator during fifteen minutes at a regular speed. Tetracaine dissolution was added over dissolution A and shacked during ten minutes until homogenized. Lidocaine base was mixed with prilocaine base in a mortar during fifteen minutes until obtaining the liquefaction and consequently the total fusion of the eutectic mixture. The eutectic mixture was added over the preceding mixture and shacked during ten minutes until complete homogenization. The resulting product was transferred to a 100 mL recipient. Hyaluronidase was mixed with the corresponding amount of distilled water and shacked with a glass stick. This dissolution was added to the preceding mixture. Dissolution E, F and G were finally added consecutively and shacked until complete homogenization. The 30 g of the resulting product was transferred to an aluminum tube.

Comparative Clinical Study Between a Topical Anesthetic Composition of the Invention and EMLA Cream: Efficacy and Adverse Effects The aim of the study was to compare the efficacy between a topical anesthetic composition of the invention versus EMLA cream. Adverse effects of both compositions were also evaluated. The study was executed during two years over a 2700 individual population with ages comprised between fifteen and sixty-five years. Different superficial dermatological procedures were made such as surface verruca extirpation, infiltrations, application of facial filling, laser or filling micropuncture of wrinkles.

The topical anesthetic composition of the invention was applied to the half of the population during thirty minutes previous to the surgical operation and without occlusion. EMLA was applied to the other half of the population during sixty minutes previous to the surgical operation and with occlusion. The degree of pain was evaluated by the patient himself with a visual analogous scale (VAS) with a minimum value (equivalent to no pain) "0" and a maximum value (equivalent to maximum pain) "10". The degree of pain was evaluated during the execution of the dermatological procedure while the evaluation of adverse effects emergence was evaluated from the anesthetic application to the end of the dermatological procedure.

Table 1 shows the results in terms of anesthetic efficacy. Tables 2 and 3 shows the results of the evaluation of adverse effects emergence during and after the application of both creams. Table 2 shows the results in terms of adverse effects of the composition of the invention and table 3 in terms of adverse effects of EMLA. In both cases few patients with adverse effects were registered, although in the case of EMLA these effects were more acute and in the case of the composition of the invention the effects were softer, of short length and with spontaneous resolution.

TABLE 1

| | degree of pain (VAS) | | | | | | | | | | |
|---|---|---|---|---|---|---|---|---|---|---|---|
| | 0 | 1 | 2 | 3 | 4 | 5 | 6 | 7 | 8 | 9 | 10 |
| EMLA | — | — | 338 | 270 | 135 | 270 | 135 | 135 | 135 | — | — |
| the composition of the invention | 702 | 162 | 149 | 162 | 108 | 67 | — | — | — | — | — |
| total patients | | | | | | 2700 | | | | | |

TABLE 2

| adverse effects | null | soft | moderate | severe |
|---|---|---|---|---|
| erythema | 89% | 10% | 1% | 0 |
| edema | 99% | 1% | 0 | 0 |
| itching | 90% | 10% | 0 | 0 |

TABLE 3

| adverse effects | null | soft | moderate | severe |
|---|---|---|---|---|
| erythema | 92.5% | 0 | 7.5% | 0 |
| itching | 97.5% | 0 | 2.5% | 0 |
| cutaneous rash | 100% | 0 | 0 | 0 |

From the results shown in the tables, it is clear that the composition of the 10 invention proves a larger efficacy and a shorter time of effect establishment versus EMLA for the same type of dermatological and/or dermoesthetic procedure. The effectiveness of EMLA is practically the half with a double time of application.

The invention claimed is:

1. A pharmaceutical composition for topical administration comprising:
   (i) a therapeutically safe and effective amount of lidocaine or of a pharmaceutically acceptable salt thereof;
   (ii) a therapeutically safe and effective amount of prilocaine or of a pharmaceutically acceptable salt thereof; and
   (iii) a therapeutically safe and effective amount of tetracaine or of a pharmaceutically acceptable salt thereof,
   wherein the pharmaceutical composition is administered without occlusion.

2. The pharmaceutical composition according to claim 1, further comprising water.

3. The pharmaceutical composition according to claim 1, wherein lidocaine or its salt on the one side, and prilocaine or its salt on the other side, form an eutectic mixture.

4. The pharmaceutical composition according to claim 1, wherein one or more of lidocaine or its salt is in an amount from about 0.5% to about 5% w/w, prilocaine or its salt is in an amount from about 0.5% to about 5% w/w, and tetracaine or its salt is in an amount from about 0.5% to about 8% w/w.

5. The pharmaceutical composition according to claim 4, wherein one or more of lidocaine or its salt is in an amount from about 0.5% to about 1.5% w/w, prilocaine or its salt is in an amount from about 0.5% to about 1.5% w/w, and tetracaine or its salt is in an amount from about 0.5% to about 8% w/w.

6. The pharmaceutical composition according to claim 5, wherein lidocaine or its salt is in an amount of about 1.5% w/w, and prilocaine or its salt is in an amount of about 1.5% w/w.

7. The pharmaceutical composition according to claim 5, wherein tetracaine or its salt is in an amount of about 4% w/w.

8. The pharmaceutical composition according to claim 5, wherein one or more of lidocaine or its salt is in an amount of about 1.5% w/w, prilocaine or its salt is in an amount of about 1.5% w/w, and tetracaine or its salt is in an amount of about 4% w/w.

9. The pharmaceutical composition according to claim 1, further comprising appropriate amounts of pharmaceutically acceptable excipients to constitute a topical formulation.

10. The pharmaceutical composition according to claim 9, wherein the excipients comprise one or a combination of two or more of at least one skin penetration enhancer, at least one spreading agent, at least one viscosity increasing agent, at least one surfactant, and at least one preservative.

11. The pharmaceutical composition according to claim 10, wherein the skin penetration enhancer includes one or both of methylpyrrolidone and dimethyl sulfoxide (DMSO).

12. The pharmaceutical composition according to claim 11, wherein methylpyrrolidone is in an amount from about 5% to about 20% w/w.

13. The pharmaceutical composition according to claim 12, wherein methylpyrrolidone is in an amount of about 10% w/w.

14. The pharmaceutical composition according to claim 11, wherein dimethyl sulfoxide is in an amount from about 0.5% to about 5% w/w.

15. The pharmaceutical composition according to claim 14, wherein dimethyl sulfoxide is in an amount of about 2% w/w.

16. The pharmaceutical composition according to claim 10, wherein the spreading agent is selected from hyaluronidases and derivatives of mucopolysaccharidases.

17. The pharmaceutical composition according to claim 10, wherein the viscosity increasing agent is selected from guar gum and a carbomer.

18. The pharmaceutical composition according to claim 10, wherein the viscosity increasing agent is in an amount from about 0.5% to about 2% w/w.

19. The pharmaceutical composition according to claim 10, wherein the surfactant is a non-ionic surfactant.

20. The pharmaceutical composition according to claim 9, wherein the topical formulation is selected from the group consisting of lotions, creams, gels, sticks, sprays, ointments and pastes.

21. A pharmaceutical composition for topical administration comprising the following components in the indicated w/w percentages: 5% of lidocaine base; 1.5% of prilocaine base; 4% of tetracaine base; 10% of methylpyrrolidone; 2% of dimethyl sulfoxide; 0.08% of topical hyaluronidase; 1.5% of guar gum; 1% of polyoxyethylenesorbitan monolaurate; 0.5% of polyoxyethylenesorbitan monooleate, and the necessary amount of water to 100%.

22. A pharmaceutical composition for topical administration comprising the following components in the indicated approximate w/w percentages: 0.5-1.5% of a lidocaine base; 0.5-1.5% of a prilocaine base; 0.5-8% of a tetracaine base; 10% of methylpyrrolidone; 2% of dimethyl sulfoxide; 0.08% of topical hyaluronidase; 1.5% of guar gum; 1% of polyoxyethylenesorbitan monolaurate; 0.5% of polyoxyethylenesorbitan monooleate, and the necessary amount of water to 100%

23. A method of use eliciting an anesthetic effect of a composition of claim 1; the method comprising:
providing a combination of lidocaine, prilocaine and tetracaine themselves or as pharmaceutically acceptable salts thereof; and, administering the composition topically without occlusion.

* * * * *